US 6,869,432 B2

(12) United States Patent
Schlapfer et al.

(10) Patent No.: US 6,869,432 B2
(45) Date of Patent: Mar. 22, 2005

(54) DEVICE FOR THE ARTICULATED CONNECTION OF TWO BODIES

(75) Inventors: Fridolin J. Schlapfer, Glarus (CH); Martin Hess, Holstein (CH)

(73) Assignee: Synthes (U.S.A.), Paoli, PA (US)

( * ) Notice: Subject to any disclaimer, the term of this patent is extended or adjusted under 35 U.S.C. 154(b) by 0 days.

(21) Appl. No.: 10/273,921

(22) Filed: Oct. 21, 2002

(65) Prior Publication Data

US 2003/0093077 A1 May 15, 2003

Related U.S. Application Data

(63) Continuation of application No. PCT/CH00/00224, filed on Apr. 19, 2000.

(51) Int. Cl.[7] .......................... A61B 17/56; A61B 17/58; A61F 2/30
(52) U.S. Cl. ........................................... 606/61; 606/73
(58) Field of Search ..................... 606/60, 61, 69–71, 606/72, 73

(56) References Cited

U.S. PATENT DOCUMENTS

| | | | |
|---|---|---|---|
| 4,422,451 A | 12/1983 | Kalamchi | 128/69 |
| 4,484,570 A | 11/1984 | Sutter et al. | 128/92 |
| 4,836,196 A | 6/1989 | Park et al. | 128/92 YM |
| 4,905,680 A | 3/1990 | Tunc | 606/69 |
| 5,002,542 A | 3/1991 | Frigg | 606/61 |
| 5,047,029 A | 9/1991 | Aebi et al. | 606/61 |
| 5,053,036 A | 10/1991 | Perren et al. | 606/69 |
| 5,057,111 A | 10/1991 | Park | 606/69 |
| 5,129,899 A | 7/1992 | Small et al. | 606/61 |
| 5,261,910 A | 11/1993 | Warden et al. | 606/61 |
| 5,380,324 A | 1/1995 | Müller et al. | 606/61 |

(List continued on next page.)

FOREIGN PATENT DOCUMENTS

| | | |
|---|---|---|
| DE | 29 33 637 | 4/1980 |
| DE | 30 27 138 A1 | 12/1981 |
| DE | 44 38 264 A1 | 3/1996 |
| EP | 0 450 075 A1 | 10/1991 |
| EP | 0 829 240 A1 | 3/1998 |
| FR | 2 640 493 | 6/1990 |
| FR | 2 726 459 | 5/1996 |
| WO | WO 88/03781 | 6/1988 |
| WO | WO 94/00066 | 1/1994 |
| WO | WO 94/06360 | 3/1994 |
| WO | WO 00/69351 | 5/2002 |

*Primary Examiner*—Kevin Shaver
*Assistant Examiner*—Anuradha Ramana
(74) *Attorney, Agent, or Firm*—Jones Day

(57) ABSTRACT

A device is provided for the articulated connection of two bodies comprising a first body, a clamping member, at least one tension member, and a second body. The first body comprises a cavity extending coaxially along a central axis. The clamping included a longitudinal axis and a coaxial bore with at least one aperture, the clamping member being complementary to the cavity and resiliently deformable in a direction orthogonal to the longitudinal axis. The at least one tension member is insertable coaxially with respect to the longitudinal axis into the bore. An axial displacement of the at least one tension member within the corresponding aperture may cause the clamping member to be expanded to contact the cavity wall and be releasably locked within the cavity. The second body is releasably connectable to the first body by means of the at least one tension member and the clamping member. A driving member is provided for displacing the at least one tension member axially relative to the corresponding aperture, wherein the driving member is connected to both the clamping member and the at least one tension member in positive axial engagement while rotatable about the longitudinal axis.

33 Claims, 7 Drawing Sheets

U.S. PATENT DOCUMENTS

| | | | |
|---|---|---|---|
| 5,470,333 A | 11/1995 | Ray | 606/61 |
| 5,501,684 A * | 3/1996 | Schlapfer et al. | 606/73 |
| 5,607,426 A | 3/1997 | Ralph et al. | 606/61 |
| 5,616,142 A | 4/1997 | Yuan et al. | 606/61 |
| 5,707,372 A | 1/1998 | Errico et al. | 606/61 |
| 5,964,762 A | 10/1999 | Biedermann et al. | 606/69 |
| 6,325,803 B1 | 12/2001 | Schumacher et al. | 606/71 |
| 6,336,927 B2 | 1/2002 | Rogozinski | 606/61 |
| 6,340,362 B1 | 1/2002 | Pierer et al. | 606/71 |
| 6,379,354 B1 | 4/2002 | Rogozinski | 606/61 |

* cited by examiner

US 6,869,432 B2

DEVICE FOR THE ARTICULATED CONNECTION OF TWO BODIES

CROSS-REFERENCE TO RELATED APPLICATION

This application is a continuation of the U.S. National Stage designation of co-pending International Patent Application PCT/CH00/00224, filed Apr. 19, 2000. The entire content of this application is expressly incorporated herein by reference thereto.

FIELD OF THE INVENTION

The invention relates to a device for the articulated connection of two bodies and in particular to a fixation device for fixating two bodies in a joint-like connection.

BACKGROUND OF THE INVENTION

In the case of various surgical implants such as articulatedly connected, multipart bone plates and osteosynthetic vertebral column fixation devices where, for example, a longitudinal carrier extending approximately parallel to the vertebral column has to be attached by means of a number of bone screws, the joint-like connections must be releasably lockable. For this purpose, resilient tension members, such as collet chucks, are used. The locking of such joint-like connections is realized by means of an expansion of these resilient tension members within a corresponding cavity with fixed dimensions. This expansion process of resilient tension members is preferably achieved by means of clamping cones or clamping wedges.

An osteosynthetic fixation device including a bone screw to be anchored in a bone, a longitudinal carrier, and a connection member by means of which the bone screw is attachable to the longitudinal carrier. One example of such a device is shown in Patent No. WO 94/00066 to Schläpfer. This fixation device comprises a resilient clamping member shaped in the form of spherical segment contained between two parallel circles which has a conical bore, and a bone screw having a male taper corresponding to the conical bore of the clamping member and a screw thread arranged in the end portion located opposite to the bone. In the connecting member, a spherical cavity for receiving the clamping member is provided which is adequately dimensioned so as to permit the spherical segment of the clamping member to be pivotably received therein. A second bore serves for receiving the longitudinal carrier. The tightening of a nut screwed over the screw thread formed in said end portion of the bone screw and supported by the clamping member causes the taper formed in the bone screw to be pulled into the inner cone of the clamping member, thus spreading said clamping member apart and pressing it firmly against the wall of the spherical cavity, whereby the connecting member and the bone screw are kept in place relative to each other.

A disadvantage common to all these connections realized by means of clamping cones consists in the difficulties encountered in releasing said connections, which often necessitates heavy hammer blows to be struck on the bone screw or the connecting member or which requires the aid of special instruments.

The invention relates to a clamping connection based on a cone mechanism or wedge mechanism which is apt to be locked and released again by means of a screw driver.

SUMMARY OF THE INVENTION

The present invention relates to a joint-like connection of two bodies comprising a first body with a cavity extending coaxially to a central axis and containing a joint pan, a clamping member with a longitudinal axis and a coaxial bore, the clamping member having a shape complementary to that of the cavity and being resiliently deformable in a direction vertical to the longitudinal axis, at least one tension member insertable coaxially to the longitudinal axis into the bore and widening axially, so that an axial displacement of the at least one tension member within the bore may cause the clamping member to be expanded and releasably locked within the cavity, a second body which is releasably connectable to the first body by means of the at least one tension member and the clamping member, and a driving member by means of which the at least one tension member is axially displaceable relative to the bore. The driving member is connected with both the clamping member and the at least one tension member in such a way as to be axially in positive engagement while rotatable about the longitudinal axis.

In a first embodiment, the device according to the invention comprises an axially positive connection rotatable about the longitudinal axis existing between the driving member and the clamping member by means of an annular shoulder formed in the driving member and of a complementary, annular groove formed in the clamping member, whereas the axially positive connection rotatable about the longitudinal axis existing between the driving member and the tension member is realized by means of a threaded connection.

In a second embodiment of the device according to the invention, the configurations of the axially positive connections rotatable about the longitudinal axis are inversed. The axially positive connection rotatable about the longitudinal axis existing between the driving member and the clamping member is realized by means of a threaded connection rotatable about the longitudinal axis existing between the driving member and the tension member is realized by means of an annular shoulder formed in the driving member and of a complementary, annular groove formed in the tension member.

In another embodiment of the device according to the invention, both of the axially positive connections rotatable about the longitudinal axis, the one between the driving member and the clamping member and the one betwen the driving member and the tension member, are realized in the form of threaded connections. Preferably, in one embodiment, one of the two threaded connections is provided with left-hand threads and the other of the two threaded connections is provided with right-hand threads. The thread pitches of the two threaded connections may be of the same amount or different amounts.

The advantages of the first and second embodiments reside in their simplicity of manipulation whereas the third embodiment, due to the two threaded connections, permits a rapid releasing and tightening and, in addition, is easy to manufacture.

The configuration of the cavity formed in the first body and of the clamping member, on which depends the type of joint-like connection to be realized, may be cylindrical or spherical, depending on the application, and is preferably shaped in the form of a spherical segment contained between two parallel circles. In the case of a cylindrical configuration, the clamping member is rotatable only about the central axis of the cavity, whereas in the case of a configuration of the cavity in the shape of a spherical segment between two parallel circles, the clamping member is rotatable about the central axis and about two other axes extending vertically thereto.

In yet another embodiment, the second body is integral with the tension member. This embodiment is specially suitable for the use of the device of the invention in a vertebral column fixation system, the second body being preferably realized in the form of a bone screw and the first body having the form of a connecting member between the bone screw and a longitudinal carrier. A configuration of the joint-like connection suitable for this purpose includes a ball-and-socket joint with a cavity shaped in the form of a spherical segment between two parallel circles.

In another embodiment, the first body is shaped in the form of a bone plate, whereas the second body forms a connecting member with another bone plate, said elements forming together a bone fixation device including two articulatedly connected bone plates. A joint-like connection suitable for this purpose has a circularly cylindrical cavity and is pivotable relative to only one axis.

The device according to the invention may in various embodiments also comprise a plurality of tension members which are displaceable coaxially to the longitudinal axis in both directions relative to the bore. In the case of embodiments including two tension members, the clamping member is preferably provided, contiguous to its end portions, with two resiliently deformable, longitudinal sections, so that one tension member may be inserted from each side into the bore.

The device advantageously provides a clamping connection based on a cone mechanism or a wedge mechanism which may be locked and, inversely, be released again by means of a screw driver and without the aid of any additional instruments.

BRIEF DESCRIPTION OF THE DRAWINGS

Preferred features of the present invention are disclosed in the accompanying drawings, wherein similar reference characters denote similar elements throughout the several views, and wherein.

DETAILED DESCRIPTION OF THE PREFERRED EMBODIMENTS

Figure 1:
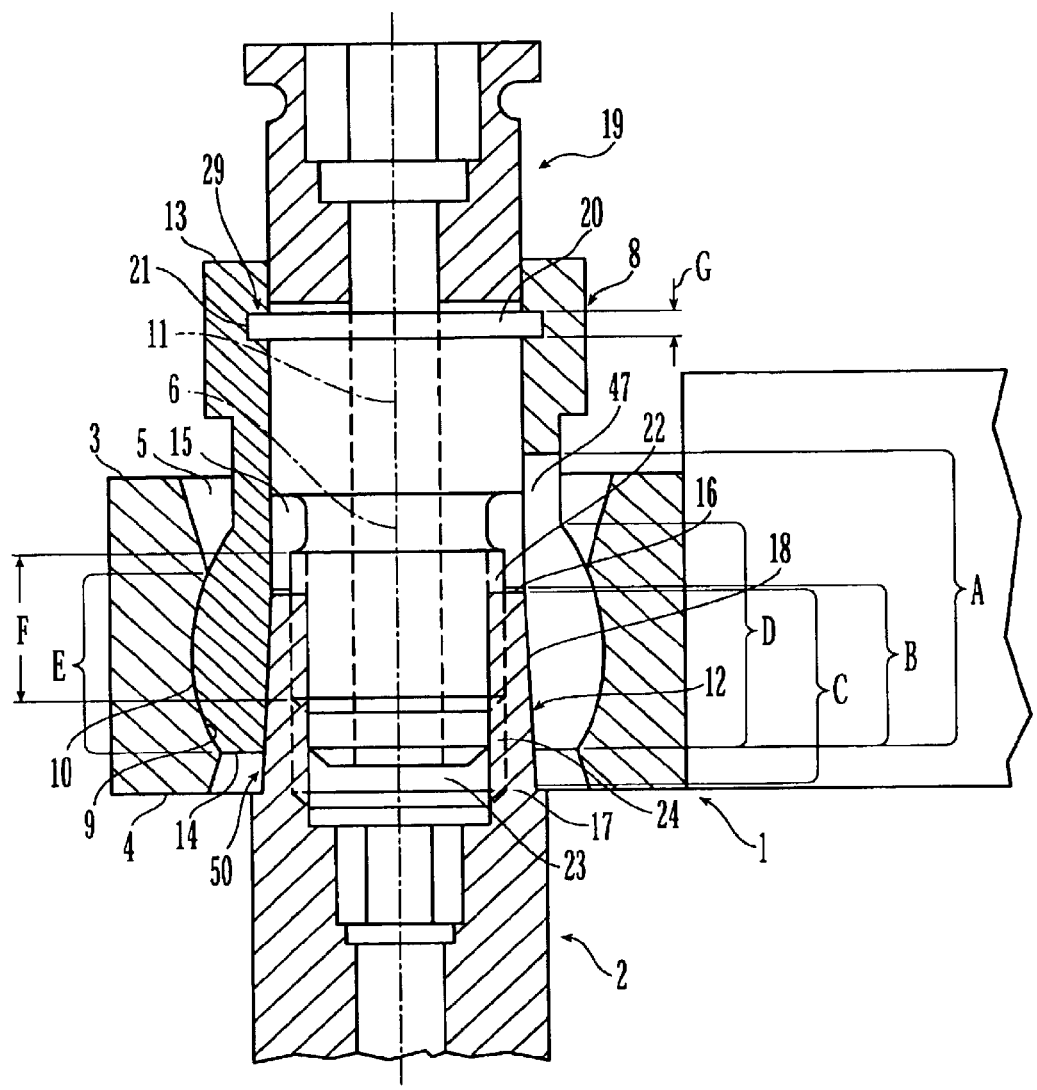
FIG. 1 is a cross-sectional view of one embodiment of the device according to the invention.

FIG. 1 shows one embodiment of the device according to the invention which comprises a first body 1 shaped in the form of a connecting member and a second body 2 shaped in the form of a pedicle screw. First body 1 includes a top surface 3, a bottom surface 4 extending parallel to the top surface 3, and a cavity 5 with a central axis 6 extending vertically to the top surface 3. Second body 2 is integral with a a tension member 12 and includes a clamping member 8, and a driving member 19 shaped in the form of a straining screw. The cavity 5 extends through the first body 1 coaxially to central axis 6 and comprises an axial longitudinal section E (N=1) which is spherically concave and rotationally symmetrical relative to the central axis 6. Corresponding to the spherically concave form of the longitudinal section E, clamping member 8 comprises a longitudinal section D (N=1), so that the clamping member 8 is rotatable within cavity 5 about the central axis 6 and about two other axes extending vertically or perpendicular or orthogonal to the central axis 6 and intersecting the center of the spherical form. Clamping member 8 additionally comprises a longitudinal axis 11, a top end 13, a bottom end 14, and, extending coaxially to the longitudinal axis 11, a bore 15 and an aperture 50 axially contiguous to each other, so that the clamping member 8 is penetrated between the top end 13 and the bottom end 14. The aperture 50 has a tapered form beginning from the bottom end 14 and extending over a longitudinal section B (N=1) and is resiliently deformable in a direction vertical or perpendicular to the longitudinal axis 11 over a longitudinal section A (N=1) containing said longitudinal section B. The resilient deformability is obtained by means of slots 47, the aperture 50 preferably comprising four such slots 47 arranged about the circumference with a radial offset of 90 degrees and penetrating parallel to the longitudinal axis 11 from the bottom surface 14.

The tension member 12 (M=1) of this embodiment is integral with second body 2, the bottom end 17 being contiguous to the second body 2. Tension member 12 is inserted with its top end 16 from the bottom end 14 into the aperture 50 formed in the clamping member 8. The tension member 12 has an axially tapered form extending towards the top end 16 over a longitudinal section C (N=1) which is complementary conical to the longitudinal section B of the aperture 50, so that the tension member 12 and the clamping member 8 form a conical clamping connection 18. A coaxial displacement of the tension member 12 within the aperture 50 causes the resilient longitudinal section A to be radially spread apart or to regain its initial position, as the tension member 12 is displaced in the opposite direction. This conical clamping connection allows the second body 2, which is integral with the tension member 12, to be releasably connected with the first body 1.

The axial displacement of the tension member 12 is made possible by turning the driving member 19, realized in the form of a straining screw, about the longitudinal axis 11. A rotatable and axially positive connection 29 between the driving member 19 and the clamping member 8 on the longitudinal section G is realized in the form of a coaxial, annular shoulder 20 formed on the clamping member 8 and of a corresponding annular groove 21 formed in the bore 15. The connection between the driving member 19 and the tension member 12, which is also axially positive and rotatable about the longitudinal axis 11, is realized in the form of a threaded engagement between an external screw thread 22 formed in the driving member 19 and a corresponding internal screw thread 24 formed in a bore 23 which penetrates into the tension member 12 from the top end 16. This threaded engagement allows the tension member 12 to be axially displaced within the clamping member 8, as the driving member 19 is rotated, while the axial forces occurring between the driving member 19 and the clamping member 8 are absorbed by the shoulder 20 of the driving member 19 located within the groove 21.

Figure 2:
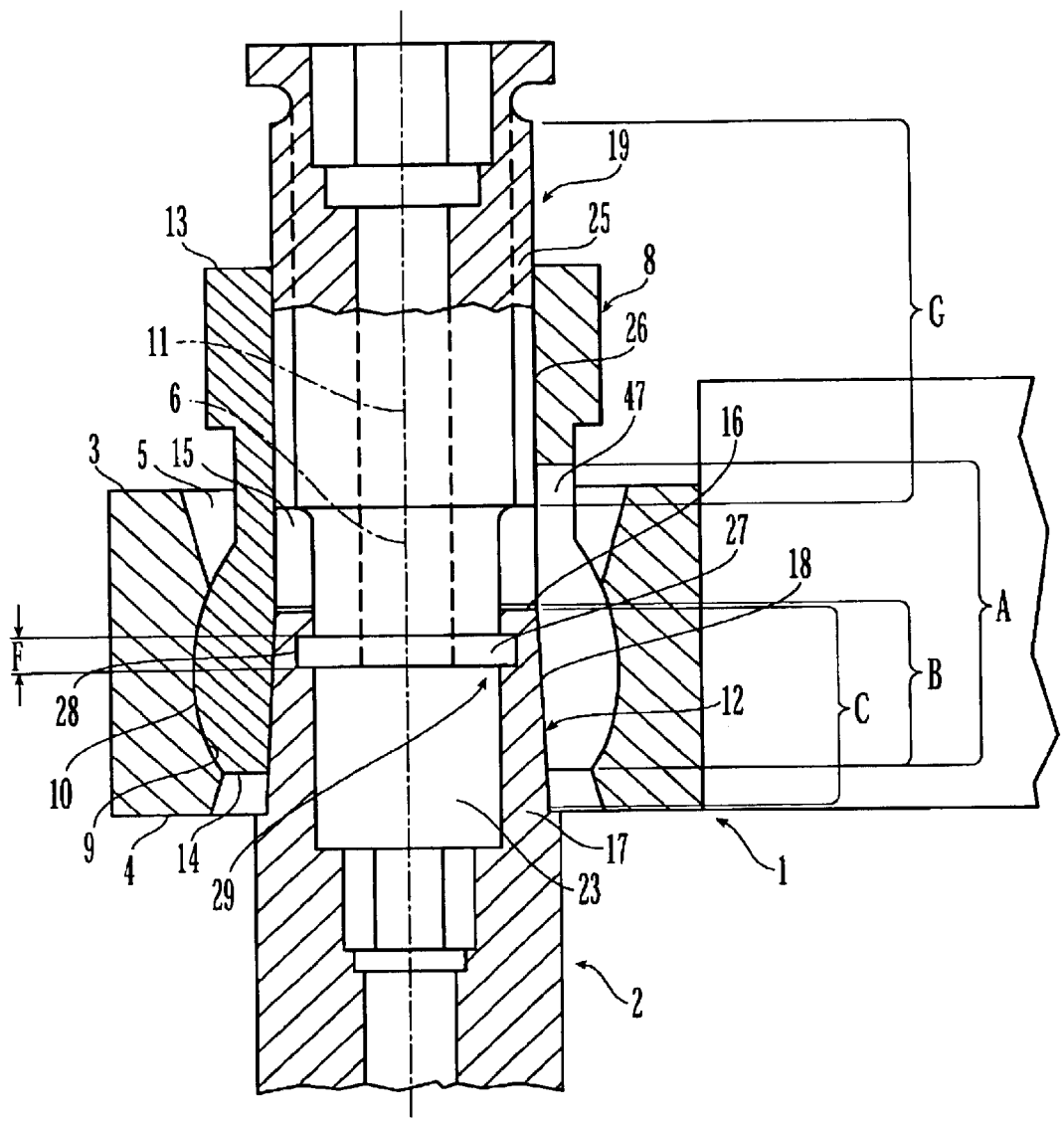
FIG. 2 is a cross-sectional view of another embodiment of the device according to the invention.

FIG. 2 shows an embodiment of the device according to the invention which differs from the embodiment shown in FIG. 1 only in so far as the axial displacement of the tension member 12 within the clamping member 8 is realized by means of a threaded connection comprising an external screw thread 25 formed in a longitudinal section G of the driving member 19 and a complementary, internal screw thread 26 formed in the bore 15. The connection between the driving member 19 and the tension member 12, which is axially positive and rotatable about the longitudinal axis 11, is realized by means of anchoring means 29 arranged in the longitudinal section F of the driving member 19 which absorb the axial forces occurring between the driving member 19 and the tension member 12. These anchoring means are realized in the form of a coaxial, annular shoulder 27 formed in the driving member 19 which is located within an annular groove 28, said groove 28 being arranged in a bore 23 which penetrates into the tension member 12 from its top end 16.

Figure 3:
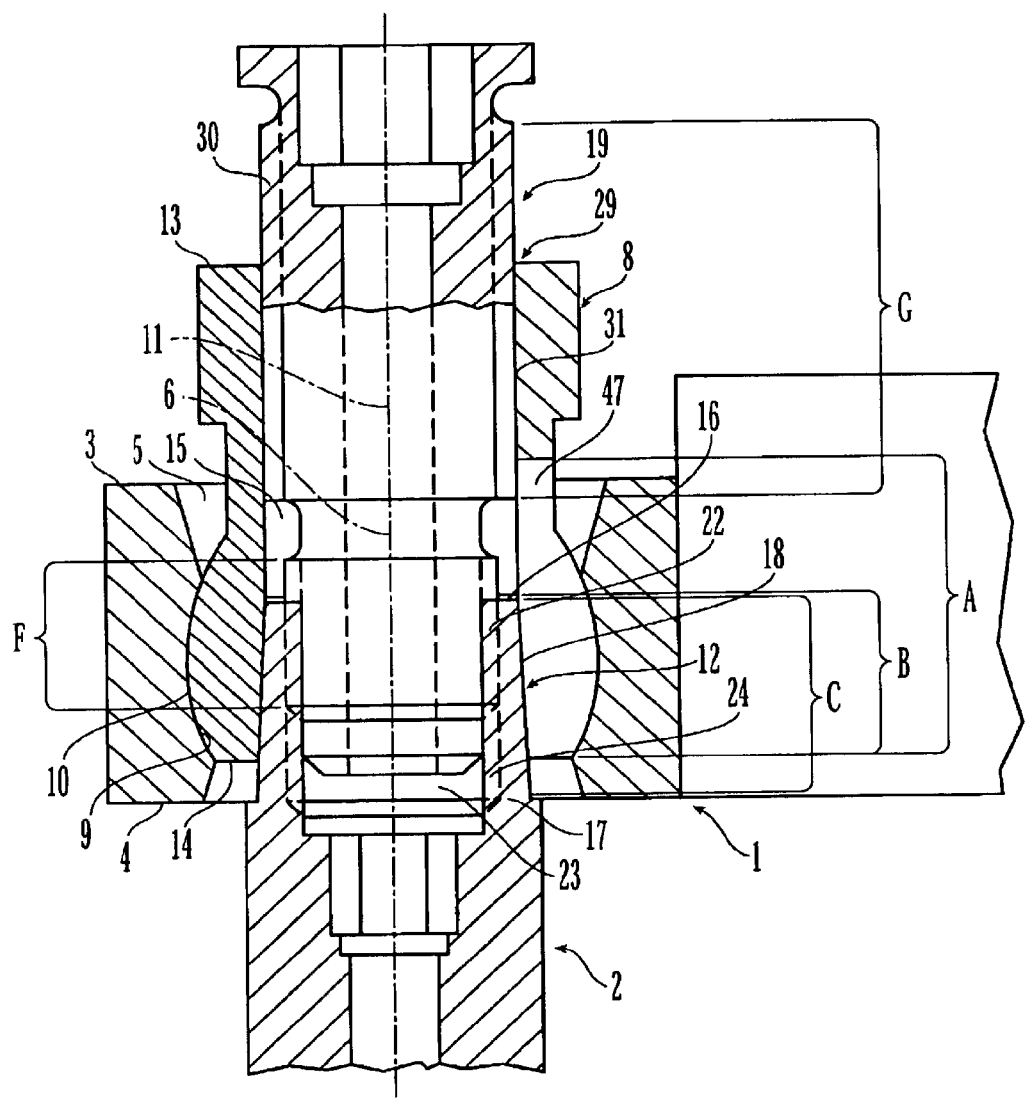
FIG. 3 is a cross-sectional view of yet another embodiment of the device according to the invention.

FIG. 3 shows an embodiment of the device according to the invention which represents a combination of the embodiments shown in FIGS. 1 and 2. On the one hand, the driving member 19 is connected to the clamping member 8 by means of a first threaded connection comprising an external screw thread 22 formed in the longitudinal section F of the driving member 19 and a corresponding, internal screw thread 24 arranged in a bore 23 of the tension member 12 which penetrates concentrically to the longitudinal axis 11 into said tension member 12 from the top end 16. Also provided is a second threaded connection comprising an external screw thread 30 formed in the longitudinal section G of the driving member 19 and a complementary, internal screw thread 31 formed in the bore 15 of the clamping member 8. The driving member 19 is connected to the clamping member 8 in such a way as to be axially in positive engagement while rotatable about the longitudinal axis 11.

Figure 4:
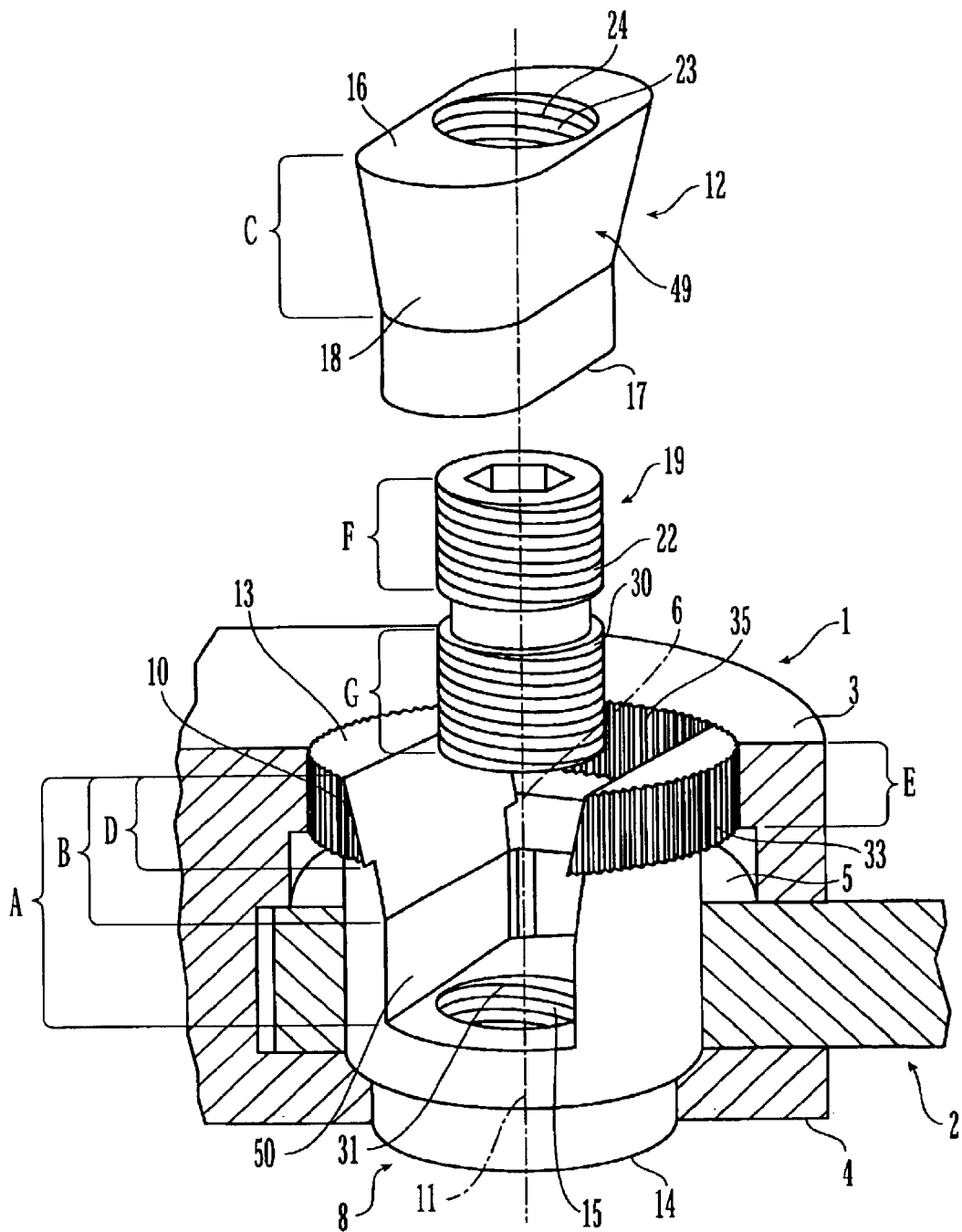
FIG. 4 is a perspective view of an embodiment of the device according to the invention for connecting two plate-like bodies.

FIG. 4 shows another embodiment of the device according to the invention comprising a first plate-like body 1 with a top surface 3, a bottom surface 4 extending parallel to the top surface 3, and a cavity 5 with a central axis 6 extending vertically to the top surface 3, a second plate-like body 2, a tension member 12, a clamping member 8, and a driving member 19 shaped in the form of a straining screw. The clamping member 8 defines an axis of rotation of a joint-like connection. The cavity 5 extends coaxially to the central axis 6 through the first body 1 and comprises a longitudinal section E (N=1) which is circularly cylindrical and rotationally symmetrical relative to the central axis 6. Corresponding to the circularly cylindrical form of the longitudinal section E, the clamping member 8 comprises a longitudinal section D (N=1), so that the clamping member 8 is rotatable about the central axis 6 within the cavity 5. The clamping member 8 comprises in addition a longitudinal axis 11, a top end 13, a bottom end 14, and, extending coaxially to the longitudinal axis 11, a bore 15 and an aperture 50 axially contiguous to each other, so that the clamping member 8 is penetrated from the top end 13 to the bottom end 14. This aperture 50 has a tapered form beginning from the top end 13 and extending over a longitudinal section B (N=1) and is resiliently deformable in a direction vertical to the longitudinal axis 11 over a longitudinal section A (N=1) containing said longitudinal section B. The resilient deformability is obtained by the fact that in the longitudinal section A, the opening 50 penetrates the clamping member 8 also in a direction vertical to the longitudinal axis 11.

Figure 5:
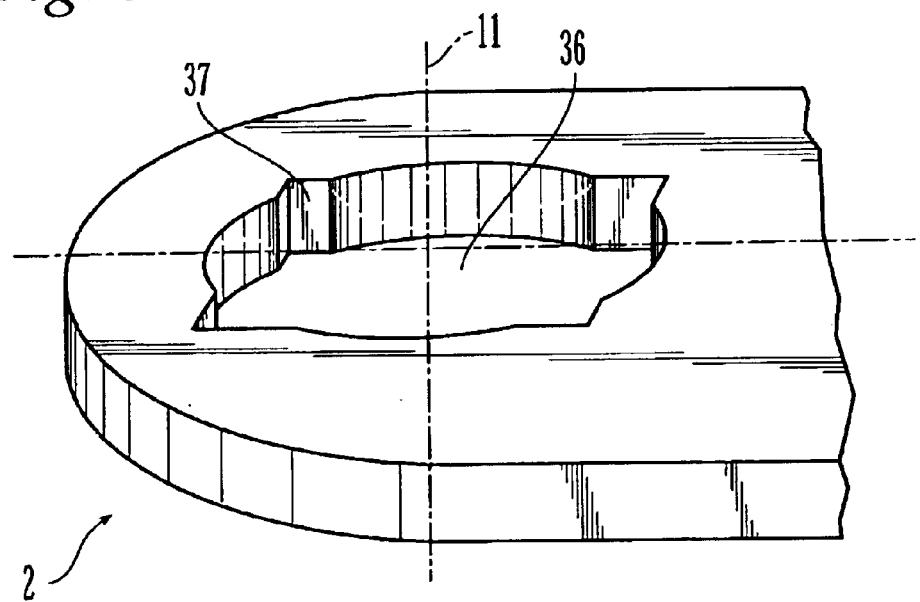
FIG. 5 is a perspective view of a detail of one of the bodies forming the embodiment of the device according to the invention shown in FIG. 4.

The tension member 12 is inserted with its bottom end 17 from the top end 13 into the aperture 50 formed in the clamping member 8. The tension member 12 has a tapered form extending parallel to the longitudinal axis 11 on a longitudinal section C (N=1) which is complementary to the longitudinal section B of the aperture 50, so that the tension member 12 and the clamping member 8 form a wedge-shaped clamping connection 49. A coaxial displacement of the tension member 12 within the aperture 50 causes the resilient longitudinal section A to be radially spread apart or to resiliently regain its initial position, as the tension member 12 is displaced in the opposite direction. From the bottom end 17 to the longitudinal section C, the tension member 12 is shaped in a square form corresponding to the square socket 37 (FIG. 5) formed in the bore 36 of the second body 2 extending coaxially to the longitudinal axis 11, which allows the second body 2 to be kept in place together with the tension member 12 relative to a rotation about the longitudinal axis 11.

The displacement of the tension member 12 parallel to longitudinal axis 11 is made possible by turning the driving member 19, realized in the form of a straining screw, about the longitudinal axis 11. On the one hand, a first threaded connection is provided comprising an external screw thread 22 formed in the longitudinal section F of the driving member 19 and a complementary, internal screw thread 24 formed in the tension member 12, and the driving member 19 is connected to the clamping member 12 in such a way as to be axially in positive engagement while rotatable about the longitudinal axis 11. The internal screw thread 24 is arranged in a bore 23 extending concentrically to the longitudinal axis 11 through the tension member 12. Also provided is a second threaded connection comprising an external screw thread 30 formed in the longitudinal section G of the driving member 19 and a complementary, internal screw thread 31 formed in the bore 15 of the clamping member 8, and the driving member 19 is connected to the clamping member 8 in such a way as to be axially in positive engagement while rotatable about the longitudinal axis 11. In order to be secured against rotation about the central axis 6, clamping member 8 is provided with an external toothing 33 formed in the longitudinal section D which is engageable with a corresponding internal toothing 35 formed in a longitudinal section E of the cavity 5.

Figure 6:
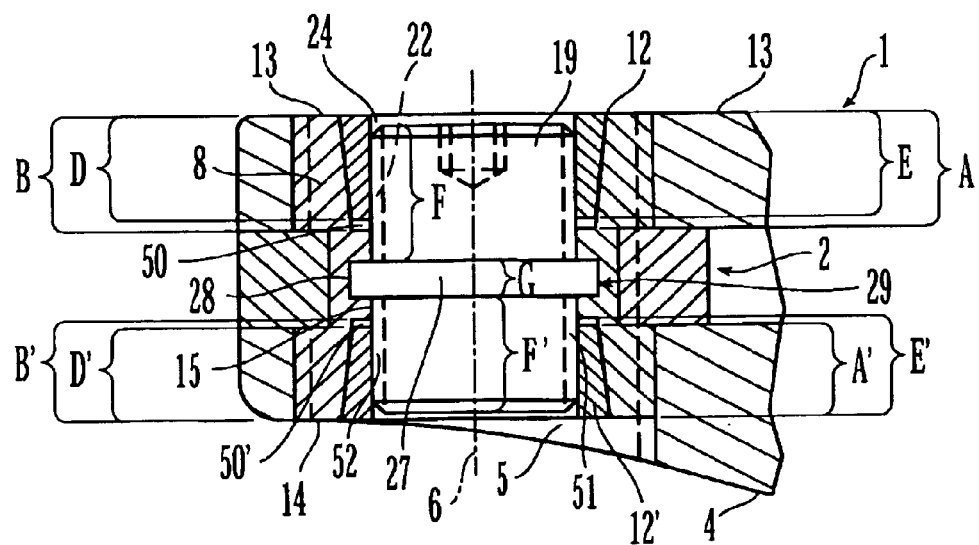
FIG. 6 is a cross-sectional view of a further embodiment of the device according to the invention.

FIG. 6 shows an embodiment of the device according to the invention which differs from the embodiment shown in FIG. 4 only in so far as it comprises a clamping member 8 with a first aperture 50 having a first, conically or wedge-shaped, tapered form beginning from the top end 13 and extending over a longitudinal section B, and a second aperture 50' having a second, conically or wedge-shaped, tapered form beginning from the bottom end 14 and extending over a longitudinal section B', as well as two tension members 12;12' which are complementary thereto. The driving member 19 is mounted within the clamping member 8 in such a way as to be axially in positive engagement while rotatable about the central axis 6. By analogy with the embodiment shown in FIG. 2, the anchoring means 29 consist of a concentric, annular shoulder 27 formed in the longitudinal section G of the driving member 19 which is mounted in a complementary, annular groove 28 formed in the clamping member 8. Both tension members 12,12' are connected to the driving member 19 by means of threaded connections, one of said threaded connections having a right-hand thread whereas the other threaded connection has a left-hand thread.

Figure 7:
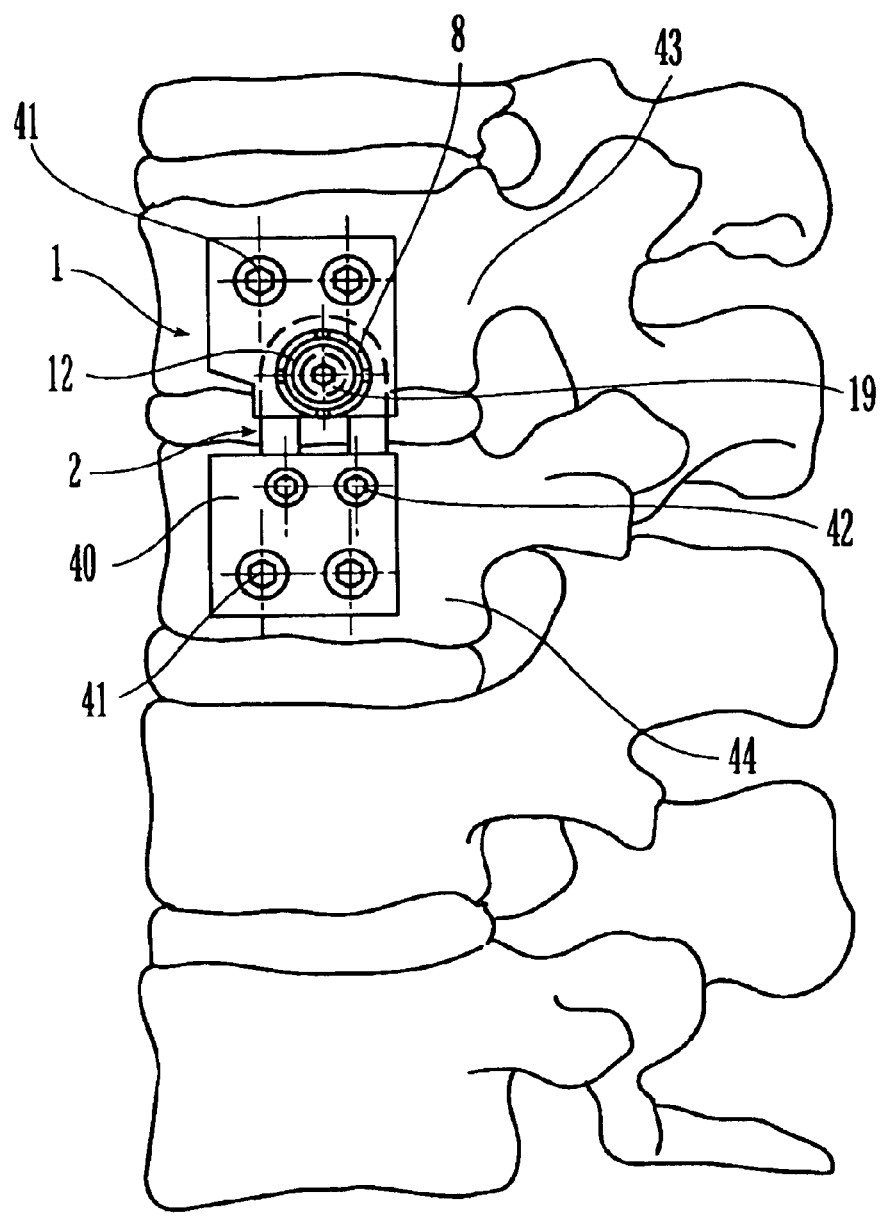
FIG. 7 is a top view of the device according to the invention shown in FIG. 6 as applied to a vertebral column.

FIG. 7 shows an application of the embodiment of the device according to the invention shown in FIG. 6 as a multipart bone plate attached laterally on a vertebral column.

The body 1 forms a first part of the bone plate attached to the cranial vertebral body 43 by means of bone screws 41, whereas the body 2 serves as a connecting member with a part 40 of the bone plate attached to the caudal vertebral body 44. By means of the clamping member 8 which is mounted in the body 1 in such a way as to be rotatable about the central axis 6 (FIG. 6) extending vertically to the surface of the vertebral body 43, the body 2 is on one side articulatedly connected to the body 1. The second part 40 of the bone plate is connected to the other side of the body 2 in such a way as to be displace-able parallel to the longitudinal axis of the vertebral column and lockable by means of two set screws 42, 80 that the bone plate allows an angular movement of the vertebral bodies 43;44 relative to each other and a displacement of said vertebral bodies parallel to the longitudinal axis of the vertebral column. The joint can be locked by means of the driving member 19.

Figure 8:
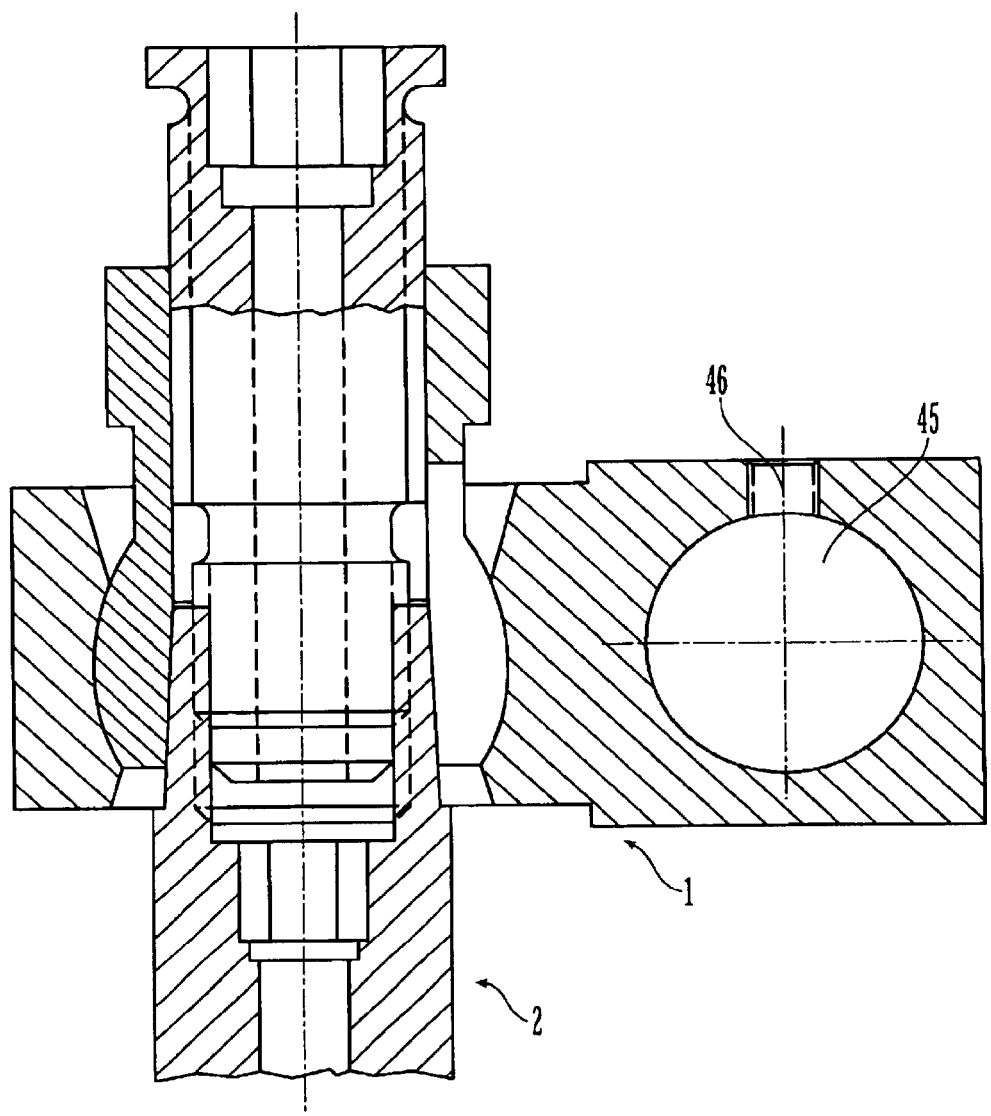
FIG. 8 is a cross-sectional view of the embodiment of the device according to the invention shown in FIG. 3 as a part of a vertebral column fixation system.

FIG. 8 illustrates the application of the embodiment of the device according to the invention shown in FIG. 3 as a connecting member within a vertebral column fixation system. The body 1 serves as a connecting member between the body 2 shaped in the form of a pedicle screw and a longitudinal carrier 45. The longitudinal carrier 45 is kept in place within the body 1 for example by means of a screw 46. One example of such a device is shown in International Patent Publication No. WO 94/00066 to Schläpfer et al.

One of ordinary skill in the art can envision numerous variations and modifications to the invention disclosed herein. All of these modifications are contemplated by the true spirit and scope of the following claims.

What is claimed is:

1. A device permitting the articulated connection of two bodies, comprising:
    a first body having a top surface, a bottom surface, and a cavity extending coaxially along a central axis and defining a cavity wall, the central axis intersecting both the top surface and the bottom surface, and the cavity extending through at least the top surface;
    a clamping member including a portion insertable within the cavity, a longitudinal axis, a top end, a bottom end, and a bore extending coaxially along the longitudinal axis and defining at least one aperture, the outside contour of the clamping member adjacent the at least one aperture shaped in a form complementary to that of the cavity and resiliently deformable in a direction orthogonal to the longitudinal axis;
    at least one tension member insertable coaxially to the longitudinal axis into the aperture, and an axial displacement of the at least one tension member within the corresponding aperture may cause the clamping member to be expanded to contact the cavity wall and be releasably locked within the cavity;
    a second body connected to the at least one tension member and releasably connectable to the first body by the at least one tension member and the clamping member;
    a driving member for displacing the at least one tension member axially relative to the corresponding aperture, wherein the driving member is connected to both the clamping member and the at least one tension member in positive engagement while rotatable about the longitudinal axis and the driving member is at least partially disposed within the clamping member.

2. The device of claim 1, wherein the clamping member has a through bore extending along the longitudinal axis.

3. The device of claim 1, wherein the clamping member comprises at least one slot extending substantially in an axial direction and connecting the aperture with the outside contour of the clamping member.

4. The device of claim 1, wherein the clamping member comprises at least two slots.

5. The device of claim 4, wherein the clamping member comprises less than 12 and at least 3 slots.

6. The device of claim 4, wherein the two slots intersect the respective aperture.

7. The device of claim 1, wherein the at least one aperture extends coaxially to the longitudinal axis.

8. The device of claim 1, wherein the at least one aperture is symmetrical about the longitudinal axis.

9. The device of claim 1, wherein the longitudinal axis and the central axis are in alignment.

10. The device of claim 1, wherein the outside contour of the clamping member in the area of contact with the wall defining the cavity is rotationally symmetrical relative to the longitudinal axis.

11. The device of claim 1, wherein the at least one tension member is coaxially displaceable in both directions along the longitudinal axis and relative to the at least one aperture by means of the driving member.

12. A device permitting the articulated connection of two bodies, comprising:
    a first body having a top surface, a bottom surface, and a cavity extending coaxially along a central axis and defining a cavity wall, the central axis intersecting both the top surface and the bottom surface, and the cavity extending through at least the top surface;
    a clamping member including a portion insertable within the cavity, a longitudinal axis, a top end, a bottom end, and a bore extending coaxially along the longitudinal axis and defining at least one aperture, the outside contour of the clamping member adjacent the at least one aperture shaped in a form complementary to that of the cavity and resiliently deformable in a direction orthogonal to the longitudinal axis;
    at least one tension member insertable coaxially to the longitudinal axis into the aperture, and an axial displacement of the at least one tension member within the corresponding aperture may cause the clamping member to be expanded to contact the cavity wall and be releasably locked within the cavity;
    a second body connected to the at least one tension member and releasably connectable to the first body by the at least one tension member and the clamping member;
    a driving member for displacing the at least one tension member axially relative to the corresponding aperture, wherein the driving member is connected to both the clamping member and the at least one tension member in positive engagement while rotatable about the longitudinal axis and the driving member contacts an interior space of the second body.

13. The device of claim 12, wherein the second body is integral with the tension member.

14. The device of claim 12, wherein the second body has an internal bore.

15. The device of claim 14, wherein the bore is configured and dimension to releasably secure the driving member.

16. The device of claim 15, wherein the bore comprises a screw thread.

17. The device of claim 12, wherein the clamping member extends outside of the first body.

18. The device of claim 17, wherein the clamping member extends rough a top surface of the first body.

19. The device of claim 12, wherein the clamping member and the driving member are operatively associated to prevent relative translational movement between the clamping member and the driving member.

20. The device of claim 19, wherein a portion of the clamping member and a portion of the driving member mesh to block relative translational movement between the clamping member and the driving member.

21. The device of claim 19, wherein the driving member is rotatable with respect to the clamping member.

22. The device of claim 19, wherein the clamping member comprises a annular recess.

23. The device of claim 22, wherein the driving member comprises a flange.

24. The device of claim 23, wherein the wherein the flange is configured and dimensioned to be received in the annular recess.

25. The device of claim 24, wherein the flange and annular recess are adapted to block relative translational movement between the clamping member and the driving member.

26. The device of claim 25, wherein the driving member is rotatable with respect to the clamping member.

27. The device of claim 19, wherein the wherein the second body comprises an orthopedic fastener.

28. The device of claim 27, wherein the wherein the fastener comprises a bone screw.

29. The device of claim 28, wherein the wherein the bone screw is a pedicle screw.

30. The device of claim 19, wherein the first body forms a connecting member between the second body and an elongate member.

31. The device of claim 30, wherein the elongate member is a longitudinal carrier.

32. The device of claim 19, wherein the first body comprises a bone plate.

33. The device of claim 32, wherein the second member forms a connecting member with another bone plate.

* * * * *